United States Patent [19]

Wertheim et al.

[11] Patent Number: 5,181,520

[45] Date of Patent: Jan. 26, 1993

[54] METHOD AND APPARATUS FOR ANALYZING AN ELECTRO-ENCEPHALOGRAM

[75] Inventors: David F. P. Wertheim, London; Rowena C. Oozeer, Northolt; Victor Dubowitz, London, all of England; John A. Connell, Reading, United Kingdom; John W. E. Brydon, Melbourne, Australia

[73] Assignee: Royal Postgraduate Medical School, London, England

[21] Appl. No.: 548,970

[22] PCT Filed: Dec. 20, 1988

[86] PCT No.: PCT/GB88/01138

§ 371 Date: Aug. 2, 1990

§ 102(e) Date: Aug. 2, 1990

[87] PCT Pub. No.: WO89/05606

PCT Pub. Date: Jun. 29, 1989

[30] Foreign Application Priority Data

Dec. 22, 1987 [GB] United Kingdom ............... 8729899

[51] Int. Cl.$^5$ ............................................. A61B 5/0476
[52] U.S. Cl. ............................. 128/731; 364/413.05
[58] Field of Search ............................ 128/731, 731; 364/413.02, 413.03, 413.05

[56] References Cited

U.S. PATENT DOCUMENTS

| | | | |
|---|---|---|---|
| 4,073,011 | 2/1978 | Cherry et al. | 364/900 |
| 4,215,697 | 8/1980 | Demetrescu | 128/731 |
| 4,254,779 | 3/1981 | Miyata et al. | 128/731 |
| 4,323,079 | 4/1982 | Demetrescu | 128/731 |
| 4,478,224 | 10/1984 | Bailey | 128/706 |
| 4,550,736 | 11/1985 | Broughton et al. | 128/731 |
| 4,616,659 | 10/1986 | Prezas et al. | 128/706 |
| 4,790,326 | 12/1988 | Mather et al. | 128/689 |
| 4,825,874 | 5/1989 | Uhlemann | 128/710 |
| 4,907,597 | 3/1990 | Chamoun | 128/731 |
| 5,029,590 | 7/1991 | Allain et al. | 128/710 |

FOREIGN PATENT DOCUMENTS 8001352 7/1980 PCT Int'l Appl. .
8705481 9/1987 PCT Int'l Appl. .

OTHER PUBLICATIONS

"Continuous 4-Channel EEG Monitoring: A Guide to Interpretation, With Normal Values, in Preterm Infants", J. A. Connell, Neuropediatrics 1987.

"Continuous 4-Channel EEG Monitoring in the Evaluation of Echodense Ultrasound Lesions and Cystic Leucomalacia", J. A. Connell, Arch. of Disease in Childhood 1987.

Primary Examiner—William E. Kamm
Assistant Examiner—Kevin Pontius
Attorney, Agent, or Firm—Nixon & Vanderhye

[57] ABSTRACT

A method and apparatus for analyzing an electro-encephalogram (EEG) are described. EEGs from the left and right sides of the head are analyzed substantially simultaneously by detecting bursts of activity having amplitudes which exceed a threshold voltage. Each burst of activity is determined to have ended, i.e. the amplitude is below the threshold voltage, when it is followed by a quiescent interval having a duration of, for example, at least six seconds. The total time of all quiescent intervals occurring within a time period, e.g. ten minutes, is then calculated and displayed. The apparatus includes a digital computer for effecting statistical analysis of total times for many consecutive time periods. The computer may also be used in generating total times. A graphical output representing total times may be generated allowing rapid access of patient progress.

22 Claims, 4 Drawing Sheets

METHOD AND APPARATUS FOR ANALYZING AN ELECTRO-ENCEPHALOGRAM

This invention relates to the analysis of an electro-encephalogram (EEG). The invention enables a computer to be used for part of the analysis.

The EEG is a long-established technique for recording spontaneous electrical brain activity using electrodes attached to the scalp of the subject. Its use in connection with monitoring the development of, for example, new born infants and especially premature new born infants has enabled the brain development of the infants to be monitored during the neonatal period. In recent years, small magnetic tape cassette recorders, such as the Oxford Medical Ltd.'s Medilog 4-24, have been used to record up to 24 hours of EEG data on two channels from very small sick babies, because the small size of the recorder has enabled it to be placed in a neonatal intensive care unit without interfering with the other apparatus used in such units. Such recorders provide enormous amounts of data for retrospective analysis, at present performed by replaying a tape on to a visual display unit at, for example, 20 or 60 times its recorded speed. This enables a 24 hour recording to be reviewed in a minimum of 24 minutes and can enable a specialist to detect abnormalities in the EEG and to take necessary remedial action. The EEG can also be printed while it is being displayed to enable the specialist to return to parts of the EEG which he suspects reveal abnormalities. An obvious disadvantage of this system is its retrospective nature, but it also suffers the disadvantage that the specialist is occupied for long periods of time reviewing the EEG traces.

Although gross abnormalities in an EEG, such as convulsions or periods of substantially no activity can be quickly detected by the specialist observing the visual display, the EEG can also reveal more subtle, though still very important, information after longer and expert analysis of the printed trace of the EEG. The visual analysis is based on several well recognized features such as the frequency and amplitude of the waveforms, the symmetry and synchrony of discharges from the right and left sides of the brain, and the presence of abnormal discharges such as convulsions.

In contrast to the normal adult EEG which shows continuous electrical activity, the EEG of premature infants is characterized by short bursts of activity, sometimes of less than 5 seconds duration, interspersed with intervals of very reduced or apparently absent electrical activity. The intervals between the bursts, which may last for 60 seconds or more, are of significance in that they can show the increasing maturity of the infant brain as the activity becomes more continuous with longer bursts and shorter intervals. Prolonged intervals relative to the age of the infant can be associated with intracranial hemorrhage or hypoxic brain damage. Obviously the more rapidly that the EEG can be analyzed, the sooner remedial action can be taken when required and possibly the severity of damage to the brain reduced.

The EEGs of older children and adults may also display intervals of reduced or apparently absent electrical activity due to the effects of drugs, anesthetics or injury.

It is an object of the present invention to provide an improved method and apparatus for the analysis of EEGs.

According to one aspect of the present invention there is provided apparatus for analyzing an electro-encephalogram (EEG) including input terminals for at least one electrical signal derived from the EEG, comparator means for comparing a representation of the magnitude of the electrical signal with a threshold level and producing an indication whenever the representation of the electrical signal reaches the threshold level, timing means for measuring the time intervals between successive indications produced by the comparator means, and producing output values representing the time intervals, selecting means for selecting only those of the output values that represent time intervals longer than a predetermined minimum time period, adding means for accumulating the selected output values representing time intervals occurring within a section of the EEG obtained during a time period of predetermined duration to produce a total value, and display means for producing a visible output comprising representations of a plurality of total values derived respectively from sections of the EEG obtained during consecutive time periods of the same duration.

When a time interval between successive indications overlaps the boundary between two time periods, the parts of it occurring in the time periods are allocated to them, respectively, unless the part of an interval which occurs in the first period is of short duration (e.g. less than 6 seconds) when that part is not included in the total for the first period.

The apparatus may also include counting means to count the numbers of intervals occurring within the time periods. The total values when divided by the numbers of intervals provide the mean interval lengths for the periods. The visible output may comprise representations of the mean interval lengths.

Preferably two channels of EEG, one obtained from the left-hand side of a patient's head and the other obtained from the right-hand side, are analyzed substantially simultaneously by the apparatus, so that the synchrony and the symmetry of the EEGs can also be monitored by the apparatus. In this case the display means may produce representations of the total values derived from both EEG channels side by side to facilitate their being compared with each other. More than two channels of EEG may be obtained from the head, and/or they may be derived from regions other than simply the left-hand and right-hand lobes; of course, these EEG signals may display more complicated tion-ships than those represented by synchrony and symmetry.

The comparator means may simply compare the amplitude of the electrical signal with a reference voltage and produce a pulse each time the electrical signal amplitude rises to reach or exceed the reference voltage, the pulses forming the indications which are applied to the timing means.

In an alternative construction the comparator means includes an analog to digital converter arranged to sample the electrical signal at a sufficiently high frequency to detect any pulses likely to occur in it and to convert the magnitudes of the samples into multi-bit digital signals. The comparison with a threshold level may be performed by comparing the multi-bit digital signals with a digital representation of the threshold level in a digital comparator. Another way of effecting the comparison is to choose the reference voltages for the analog to digital conversion so that one of them corresponds to the threshold level; the resulting digital signals have 1's in places at or above that corresponding to the threshold level only if the electrical signal is at or above the threshold level, so that the comparison can be effected by detecting a "1" in the place at or about that corresponding to the threshold level.

The timing means, selecting means and adding means may be provided by a digital computer programmed so as to execute the required operations on the indications produced by the comparator means to derive from those indications the required total values.

If the timing means, selecting means and adding means are provided by a suitably programmed digital computer, then the multi-bit digital signals obtained from the analog to digital converter included in the comparator means may be applied to the computer as inputs, and the computer may also be programmed to determine whether the digital inputs obtained from the converter are above or below the threshold level.

Where a digital computer is present, for example, as mentioned above, it may be programmed to process the total values obtained from the adding means to produce a graphical display of a form readily assimilable by a specialist.

The EEG channel from which the electrical signal is derived may be recorded on a suitable magnetic tape and replayed at a much higher speed than that at which it was obtained from the patient. For example, the EEG signal may be recorded directly from the patient for a period of 24 hours and replayed to the analyzing apparatus over a period of 24 minutes. Of course, adjustment must be made for the compression of the time scale in setting the time intervals used in the analysis.

Alternatively, the EEG signals obtained from the patient may be applied directly to the apparatus so that it can be used in the "on-line" monitoring of the patient. The apparatus may be arranged to generate alarm signals in response to features of the EEG which might require some kind of remedial action.

The apparatus, especially if it is includes a suitably programmed digital computer, may be able to process an EEG obtained directly from a patient very much more rapidly than events are likely to occur in the EEG. Therefore EEGs from several patients may be multiplexed to a single apparatus which may also be arranged to produce a separate display for each patient and to monitor the EEGs for features requiring remedial action.

According to a second aspect of the present invention there is provided apparatus for analyzing an electroencephalogram (EEG) including input terminals for at least one electrical signal derived from the EEG, sampling means connected to the input terminals to sample the electrical signal at regular time intervals and hold the sample, analogue to digital conversion means connected to receive the samples held successively by the sampling means and producing therefrom digital outputs representing the magnitudes of the samples, a digital computer programmed to receive the digital outputs in succession from the analogue to digital conversion means, to compare each digital output with a threshold value and, only if the digital output is greater than the threshold value, to read from a timer a representation of the time interval since the sample following the last one exceeding the threshold value, to accumulate a total of the time intervals of a certain minimum duration read from the timer during a time period of predetermined duration, and to output a representation derived from the totals accumulated during consecutive time periods, and display means responsive to the output of the digital computer. The representation may be of the mean interval duration.

Preferably the apparatus is arranged to analyze at substantially the same time several channels of EEG obtained respectively from the left and right sides of the head of a patient and to produce on the display means corresponding displays side by side. It may be arranged to analyze more or other channels of EEG derived from the patient.

The reading of the time interval from the timer may be followed immediately by resetting the timer to zero and re-starting it when next a sample is below the threshold value.

The digital computer may also be programmed to store local maximum and minimum values represented by the digital outputs of the analog to digital conversion means for analysis and to output to the display means data resulting from that analysis.

The digital computer may also be arranged to calculate the mean of the squares of the sample amplitudes during a time period and count the number of time intervals of the minimum duration or longer which occur in a time period. Statistical analysis of the data may permit, for example, the correlation of the squares of the amplitudes of the left and right EEGs and the correlation of the squares of the amplitudes with the durations of the time intervals.

According to a third aspect of the present invention there is provided a method of analysing an electroencephalogram (EEG) in which the EEG is represented by a plurality of digital values respectively corresponding to the amplitude of the an EEG signal at a succession of instants spaced apart by predetermined equal time periods, the method comprising the following steps: comparing the digital values sequentially with a threshold value and indicating whether the digital values are larger or smaller than the threshold value, producing a representation of the time interval for which successive digital values are smaller than the threshold value, summing the representations of the time intervals having at least a certain minimum duration, the representations being produced during an extended time period to provide a total for each of a plurality of consecutive extended time periods, and producing an output display dependent on the totals.

The measurement of time durations may be related to a clock oscillator used to control the application of the digital values for comparison.

The output display may include a graphical display of the values of a plurality of the totals represented on a rectangular or other type of coordinate system.

The method may include the determination of the mean of the squares of the digital values occurring during an extended time period.

The method may also include the counting of the number of time intervals added to the total during an extended time period, and the calculation of the mean of the time intervals during the period.

An example of the invention will now be described with reference to the accompanying drawings, of which:

Figure 1:
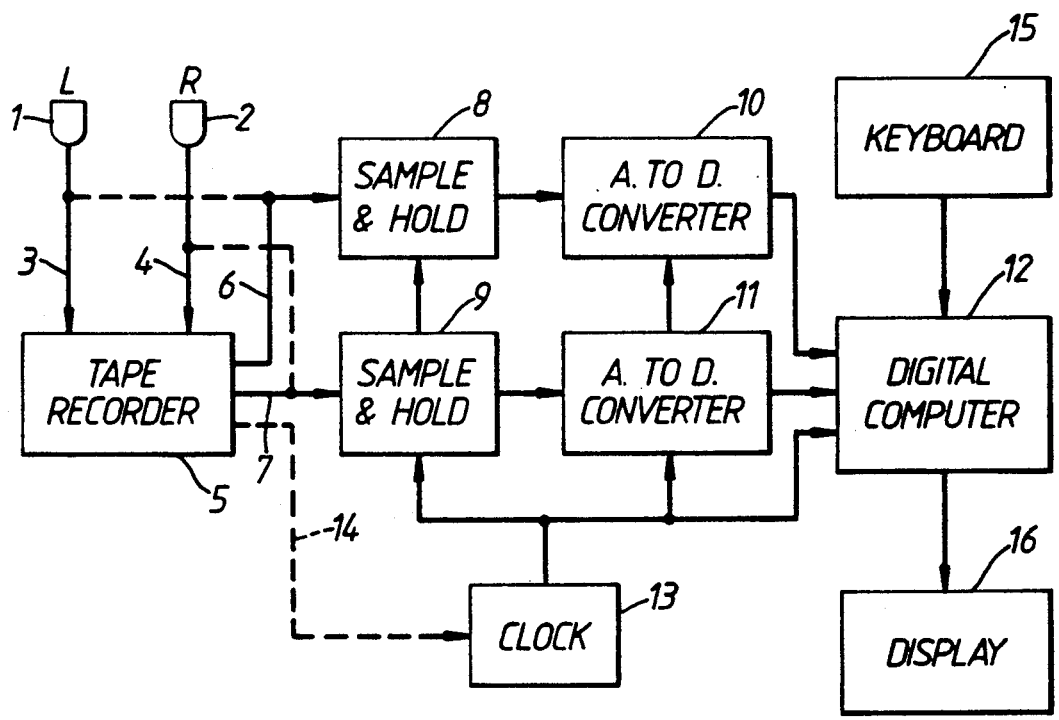
FIG. 1 is a block diagram of one form of the apparatus.

Referring now to FIG. 1, the apparatus shown has probes 1 and 2 respectively for connection to the left and right sides of the head of a patient. The probes may be connected through suitable isolation circuits (not shown) to the inputs of amplifiers (also not shown), the outputs of which are connected through conductors 3 and 4 respectively to two inputs of a magnetic tape recorder 5 for recording the channels of the EEG picked up by the probes. On playback, the recorder 5 produces left and right outputs on conductors 6 and 7 which are applied to sample and hold circuits 8 and 9 respectively. The outputs of the sample and hold circuits 8 and 9 are fed to analog to digital converters 10 and 11 respectively which supply binary coded digital values to a digital computer 12. A clock 13 is connected to supply timing pulses to the sample and hold circuits 8 and 9, the analog to digital converters 10 and 11 and the computer 12. The clock 13 may be synchronized with the playback of the tape in the recorder 5 via a connection 14. The computer 12 is connected to a keyboard 15 and to display apparatus 16 which may, for example, include a cathode ray display tube and a printer.

Optional direct connections from the probes 1 and 2 to the sample and hold circuits 8 and 9 are indicated by broken lines. Such direct connections enable the apparatus to analyze the EEGs on-line.

The use of sample and hold circuits may be unnecessary for certain types of analog to digital converters.

Figure 2:
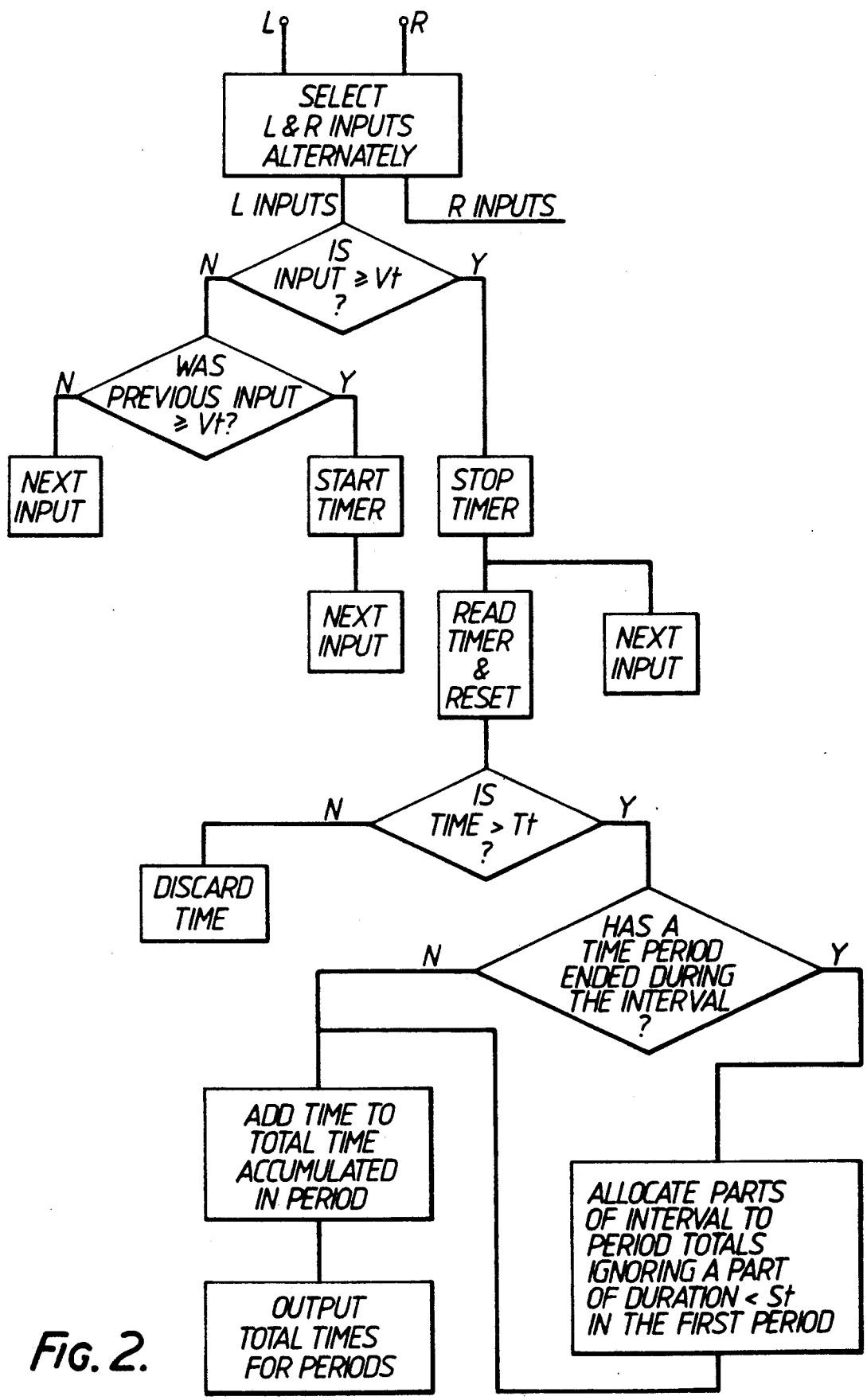
FIG. 2 is a flow diagram of an example of some of the operations performed by the computer in the apparatus of FIG. 1.

The program of the digital computer 12 includes a part represented by the flow diagram of FIG. 2. From FIG. 2 it can be seen that the program is arranged to select inputs from the left and right channels of the EEG alternately. Both sets of inputs are treated in the same way, the operations on the left EEG channel being shown. The magnitudes of the successive inputs are compared with a threshold value Vt. If an input is less than the threshold value the previous input relative to the threshold is taken into account. If the previous input is smaller than the threshold value no further action is taken, but if it is greater than the threshold value a timer in the computer is started. The timer is stopped when the next input having a magnitude greater than the threshold value occurs. The time is then read and the timer reset to zero. The time read is compared with a threshold time Tt and if it is less then that time it is discarded, but if it is greater it is added to a total time being accumulated for a period. In one example the period is 10 minutes which as explained below may be represented by 10 seconds of clock time within the computer. If the interval recorded by the timer crosses the boundary of one period into the next, the time duration of the interval is allocated to both periods according to how it was divided by the boundary between the periods. If, however, the part of the interval to be allocated to the first of the periods is less than a time St (say 6 seconds) then that part of the interval is not included in the total for that period. The total times accumulated for the periods are produced as an output and the means accumulating the time for each period is reset ready for the next period.

The apparatus of FIG. 1 using the program represented by FIG. 2 analyzes left and right channels of the EEG of a patient using measurement of the interval of time between bursts as a basis.

The aggregates of the interval times for a succession of periods produced in this way are displayed in a form easily assimilated by a specialist, so that he can tell very quickly whether or not the brain activity is normal. The mean of the interval times for a period may be displayed instead; for this purpose the computer could count the number of intervals in each period.

Figure 3:
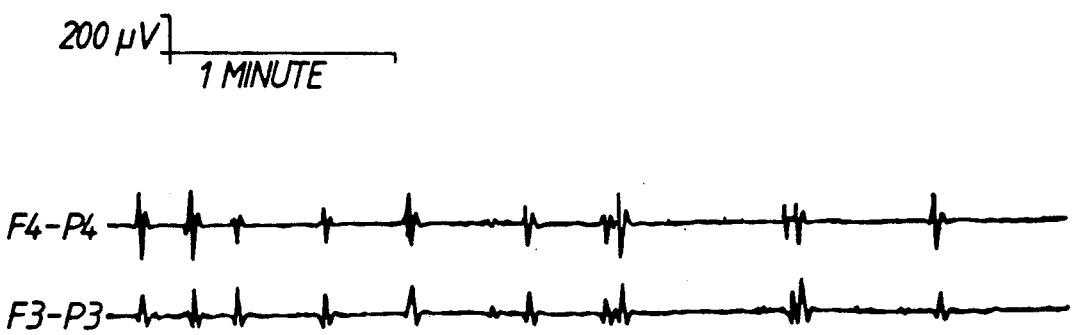
FIG. 3 shows the left and right channel traces of the EEG of a premature infant of about 28 weeks post menstrual age.

FIG. 3 shows sections of left and right EEG channel traces for an infant having post menstrual age of about 28 weeks. Consideration of FIG. 3 reveals that both left and right EEGs consist of bursts of electrical activity followed by intervals during which the activity is of much smaller amplitude or is apparently absent.

The bursts in both EEG traces are similar in form and duration and occur more or less simultaneously. If the bursts are not similar and substantially simultaneous, this may be an indication of some kind of disorder. EEG channels from other parts of the head may have other relationships.

Figure 4:
FIG. 4 shows the left and right channel traces of the EEG of a premature infant of about 32 weeks post menstrual age.

FIG. 4 shows the EEG traces for an infant 3 to 4 weeks older than that from which the EEG traces of FIG. 3 were obtained. It can be seen from FIG. 4 that the bursts of activity which are of longer duration sometimes continuing for a minute or more without significant interruption and the duration of the intervals between bursts is considerably reduced.

A difficulty encountered in analyzing EEG channel signals of the kind shown in FIG. 3 lies in determining when a burst of activity has ceased and when the next burst has started so that the duration of the interval between bursts can be determined accurately. The technique adopted in the apparatus of FIG. 1 involves noting every time that the sample exceeds a threshold value, the value used corresponds to an EEG voltage of approximately +25 microvolts. Whenever an input first falls below the threshold value after having been above it a counter is started, but if an input exceeding the threshold value occurs within a short time of the counter being started it is judged that the input is part of the same burst of activity as the earlier ones and the input below the threshold value did not mark the beginning of an interval between bursts. The threshold time used for this purpose is 6 seconds. The counter having been started is stopped by the next input exceeding the threshold value and if the time is less than the threshold time the output of the timer is discarded. If, on the other hand, the next input exceeding the threshold occurred more than 6 seconds after the counter being started, it is considered to be part of a different burst and the output of the timer is retained. The retained time is added to the total of other intervals previously occurring during a measurement period until the end of that period. The measurement period is, as mentioned above, 10 minutes of real time. Each time the counter is stopped and the time recorded is read out, the counter is immediately reset to zero.

An alternative method of measuring the interval durations is to stop, read, reset and restart the timer at each occurrence of an input exceeding the threshold value. This would have the effect of increasing each measured interval duration by the time between successive samples, which may, if desired, be compensated either by subtracting that time from the time recorded or by delaying the starting of the time appropriately.

As mentioned above, the EEG channel signals from opposite sides of the patient's head may have bursts of activity which are similar in form and duration and which occur more or less simultaneously. This phenomenon is termed "synchrony". The apparatus can be arranged to check two or more channels of the EEG for synchrony, by monitoring the finish and/or start times of the intervals between bursts (indicating the starts and/or finishes of the bursts) in the different channels and measuring the differences in time of occurrence and/or duration of the bursts. If the bursts in the channels occur within a certain time, say 2 seconds, they are counted as synchronous and if they are separated by more than that time they are counted as asynchronous. The numbers of synchronous and asynchronous bursts occurring in each time period are counted and displayed.

Occasionally a single electrical noise pulse is picked up by a probe because of the sensitivity of the apparatus to small voltages; the apparatus may be programmed to ignore such a pulse in comparing the EEG channel of one side with that of the other. On the other hand, the technique described above for identifying the start and finish of an interval will recognise a single pulse as a burst and divide the interval into two. Although this can lead to a slight reduction in the aggregate of interval times, it is not likely to result in a significant change in the average value of the aggregates of interval times as displayed.

In order to utilize more fully the processing power of the computer and to enable it to analyze, for example, 24 hours' recording of EEG channel signals in a relatively short period of time, the recorder 5 is arranged to replay the tape at a much higher speed than that at which the recording was made. Typically, the recordings are replayed at 60 times the speed at which they were made so that inside the computer the time periods referred to above are divided by a factor of 60. Even greater speed-up of the recorded EEG signals may be employed, provided that the replay system is capable of operation at the speeds and the frequencies involved.

The EEG signals may be speeded up after sampling and conversion to digital form by storing the samples in a random access memory at one rate and reading them out at another rate. This may be done instead of or additionally to the speeding up of the magnetic tape recorder.

Although in general the clock oscillator in the computer and the tape recorder speeds will be sufficiently stable to permit the computer clock oscillator to provide an accurate measurement of the real time periods in the EEG as originally recorded and to act as a reference for the operations executed by the computer as described above, when the EEG has been pre-recorded and is played back by the tape recorder it may be desirable to adjust the frequency of the clock oscillator in accordance with the rate at which the EEG signal is read out by the recorder. This control is represented by the broken line 14 in FIG. 1 and may involve the use of a timing track on the tape producing pulses which adjusts the frequency of the clock oscillator 13 shown to be external to the computer for convenience of illustration. This oscillator determines the frequency of sampling by the sample and hold circuits 8 and 9 and the operation of the analogue to digital converters 10 and 11. The oscillator 13 provides the time reference for the counter and the other timed operations which are carried out in the computer.

It has been found that in practice the use of a voltage threshold of approximately +25 microvolts and a threshold time of 6 seconds as described above to distinguish between bursts and intervals between bursts used in the manner described above, results in a mean duration for the intervals which corresponds very closely to that obtained by a specialist measuring the time intervals directly from the EEG traces. It would of course be possible to use other values for the threshold value and the threshold time, although it is likely that such values will be close to the ones given above.

The apparatus of FIG. 1 may be constructed in the form of a purpose-built microcomputer with additional circuitry for use as a monitoring unit for an individual patient sampling continuously the EEG signals obtained directly from the patient. In such a case the probes 1 and 2 are connected directly through amplifiers to the sample and hold circuits 8 and 9 and the time periods in the computer adjusted to the real time values rather than the accelerated time values used when the computer is analysing a speeded-up replay of recorded EEG signals. The tape recorder 5 may still be retained to record the EEG signals as well, so that they are available for subsequent examination by a specialist if necessary.

Advantageously but not necessarily exclusively when the computer is used to analyze the EEG signals received directly from the patient, the computer may be arranged to identify alarm conditions which may occur, for example, if the intervals between bursts become excessively long, (longer than 90 seconds, say) or if the aggregate of the intervals between bursts in a 10 minute period exceeds a predetermined proportion of that period depending on the condition of the patient. Other conditions requiring attention from the specialist could also be detected, for example if bursts occur in the EEG signal from one side of the head and are not matched by bursts from the other side at substantially the same time (excluding isolated noise pulses). The samples received by the computer can also be tested to see whether the amplitude of the bursts is above or below a pre-set limit, and also to monitor the mean duration of the intervals.

Instead of using a sample and hold circuit feeding an analog to digital converter to produce the digital inputs to the computer from an EEG signal, the EEG signal may be applied to a simple analog threshold circuit producing a "1" output whenever the amplitude of the EEG voltage exceeds a threshold value, say 25 uV, and a "0" output at other times. The computer may be programmed either to poll the output of the threshold circuit repeatedly at short intervals to detect the 1's and 0's or to receive the transistions from "0" to "1" and "1" to "0" as interrupts. When the computer receives a "1" to "0" input it starts the timing counter as described above to determine whether or not it marks the start of an interval between bursts. Such simpler apparatus can produce a display of the aggregates of interval times and the mean interval durations, but cannot monitor the actual voltages occuring in the EEG signals.

Figure 5:
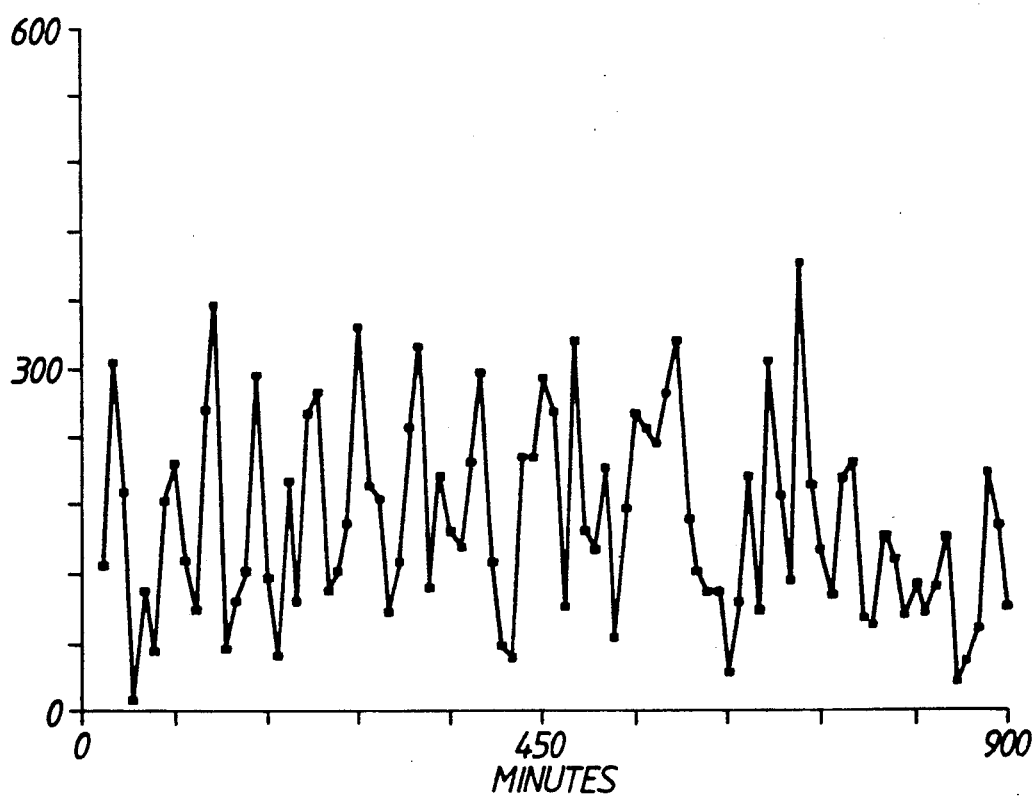
FIG. 5 is a plot of the aggregates of the intervals between bursts in successive periods of an EEG channel trace of the kind shown in FIG. 3.
Figure 6:
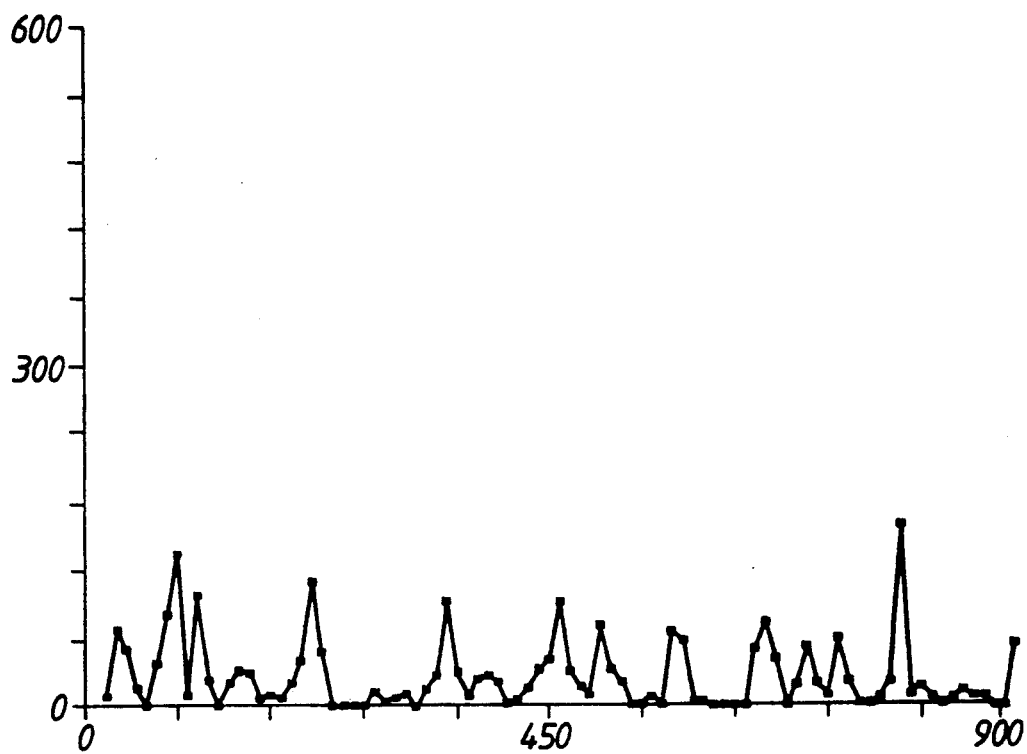
FIG. 6 is a plot of the aggregates of the intervals between bursts in successive periods of an EEG channel trace of the kind shown in FIG. 4.

The form of the display produced by the computer is preferably graphical so that, if the aggregates of the interval times during the periods lie outside an expected range for the age of infant concerned, this fact will be immediately apparent to a specialist and he can initiate remedial action without delay. FIGS. 5 and 6 show a possible form for the display in which the aggregate times are plotted as points on a graph against the minutes of the periods to which they relate.

A glance at FIG. 5 shows that the average value of the aggregate times varies between 100 and 200 seconds with a maximum of about 360 seconds and a minimum of about 10 seconds. This appears to be fairly typical for an infant of 28 weeks post menstrual age.

The infant of which FIG. 6 is a display of the aggregate times is of 32 weeks post menstrual age. It can be seen that for many periods the aggregate times are zero and the maximum aggregate time is about 150 seconds.

Figure 7:
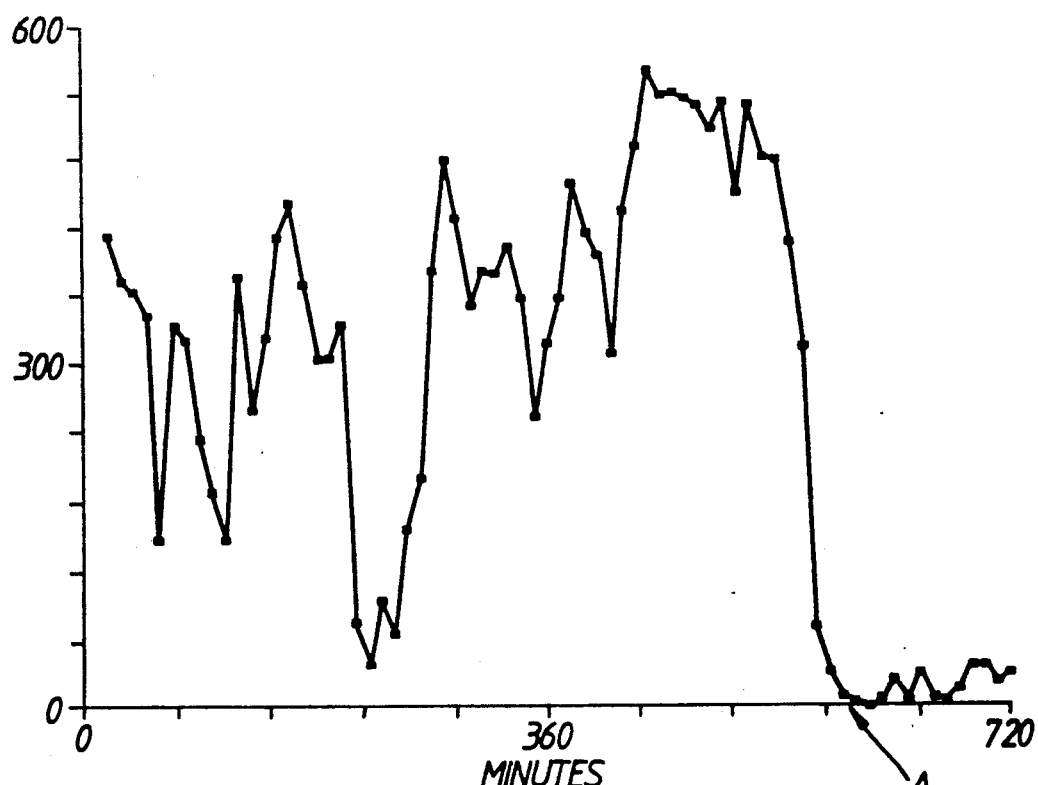
FIG. 7 is a plot similar to FIGS. 5 and 6 showing the change brought about by rectification of hypoxia in an infant of about 32 weeks post menstrual age.

A particular use of the apparatus is revealed by FIG. 7 which shows a display of the same type as is shown in FIGS. 5 and 6, but for an infant of about 32 weeks post menstrual age. The normal display obtained from the apparatus for an infant of this age is shown in FIG. 6, and it is immediately apparent that to the left of the position marked by the arrow A in FIG. 7 the aggregates of the intervals are very much higher than they should be for a healthy infant. This occurred when the infant was hypoxic, and when the oxygen supply was increased at the time indicated by the arrow A it can be seen that the aggregates immediately came down to the sort of values displayed by FIG. 6.

The analyzed or partly analyzed data may be stored in a semipermanent memory, such as a magnetic disc, for subsequent display without any further processing or for further analysis and display.

The display may take other forms and may also include indications of the following in graphical and/or numerical form for each side or for both sides of the brain:
1. the peak value of a burst in the EEG as represented by a sample.
2. the length of the longest interval time in each period.
3. the number of intervals in each period.
4. the mean of the interval times in each period and for the entire EEG.
5. difference in amplitude and timing between the bursts in the EEGs of the two sides.
6. correlation between right and left mean squares of the amplitudes.
7. correlation between the squares of the amplitudes and the interval length.

We claim:

1. Apparatus for analyzing an electro-encephalogram (EEG) in which electrical signals derived from the EEG are applied to a threshold detector and threshold output signals are examined for a particular kind of brain activity, comprising:
   input terminals for receiving at least two electrical signals respectively representing at least two channels of EEG which may be derived from different sides of a patient's head, wherein the two electrical signals are analyzed substantially simultaneously;
   timing means for measuring time intervals between successive output signals produced by the threshold detector and for providing output values representing the time intervals;
   selecting means for selecting only those output values that represent time intervals longer than a predetermined minimum time;
   adding means for accumulating the selected output values representing time intervals occurring within a section of the EEG obtained during a time period of predetermined duration to produce a total value; and
   display means for producing a visible output including a plurality of total values derived respectively from the EEG channels side by side obtained during consecutive time periods of the predetermined duration.

2. Apparatus according to claim 1 further comprising:
   counting means for counting the number of selected time intervals longer than the predetermined minimum time occurring within time periods of predetermined duration, and
   means for dividing the total values produced for the different time periods respectively by the numbers of selected intervals occurring within those time periods to provide indications of the mean length of the selected intervals in those time periods for display by the display means.

3. Apparatus according to claim 1 wherein two channels of the EEG are derived from opposite sides of the patient's head and the analysis of the two electrical signals includes comparing the times of occurrence when the electrical signals reach the threshold level, counting the occurrence times which are substantially simultaneous and those which are not substantially simultaneous within each time period, and displaying the count totals.

4. Apparatus according to claim 1 wherein the timing means, the selecting means and the adding means are provided by a digital computer programmed to process the outputs produced by the threshold detector to derive the required total values.

5. Apparatus according to claim 4 wherein the computer is programmed to cause the display means to display the total values in a graphical form readily assimilable by a specialist.

6. Apparatus according to claim 1 wherein each electrical signal derived from the EEG is fed through a signal channel including a magnetic tape recording means for recording the electrical signal on a magnetic tape at a first speed and for replaying the recorded signal from the magnetic tape at a second speed faster than the first speed to produce a modified electrical signal, the durations of the time periods and intervals being selected to allow for any change in speed of the electrical signal resulting from the recording and replaying.

7. Apparatus according to claim 6 wherein the magnetic tape recording means records the electrical signal derived from the EEG over a period of about 24 hours and replays the record in about 24 minutes.

8. Apparatus according to claim 1 wherein each channel of the EEG is applied via isolation circuitry from the patient to the input terminals.

9. Apparatus for analyzing an electro-encephalogram (EEG) in which at least one electrical signal derived from the EEG is applied to a threshold detector and the output is examined for a particular kind of brain activity, comprising:
   analog to digital conversion means, wherein the electrical signal derived from an EEG channel is converted to digital form by the analog to digital conversion means at a sampling frequency sufficiently high to detect pulses in the electrical signal and the resulting digital signal is applied to a comparator means for comparison with a digital threshold signal;

timing means for measuring time intervals between successive output signals produced by the threshold detector and for providing output values representing the time intervals;

selecting means for selecting only those output values that represent time intervals longer than a predetermined minimum time;

adding means for accumulating the selected output values representing time intervals occurring within a section of the EEG obtained during a time period of predetermined duration to produce a total value;

display means for producing a visible output including a plurality of total values derived respectively from sections of the EEG obtained during consecutive time periods of the predetermined duration;

wherein in the comparator means the electrical signal derived from an EEG channel is converted to digital form in an analog to digital converter, one of the converter reference voltages being at the threshold level, and comparison is effected by detecting non-zero digits in the digital signal at least as significant as that corresponding to the threshold level.

10. Apparatus according to claim 9 in which the timing means, the selecting means and the adding means are provided by a suitably programmed digital computer, wherein the digital signal from the analog to digital conversion means is applied to the computer as an input.

11. Apparatus according to claim 10 wherein the digital computer is programmed to compare the digital input signal with a threshold level.

12. Apparatus for analyzing electro-encephalograms (EEGs) in which electrical signals derived from several channels of EEG are applied to a threshold detector and detector output signals are examined for a particular kind of brain activity, comprising:

means for multiplexing electrical signals derived from several channels of EEG from several patients to the input terminals;

timing means for measuring time intervals between successive output signals produced by the threshold detector and for providing output values representing the time intervals;

selecting means for selecting only those output values that represent time intervals longer than a predetermined minimum time;

adding means for accumulating the selected output values representing time intervals occurring within a section of the EEG obtained during a time period of predetermined duration to produce a total value; and display means for producing a visible output including a plurality of total values derived respectively from sections of the EEG obtained during consecutive time periods of the predetermined duration.

13. Apparatus for analyzing an electro-encephalogram (EEG) using the amplitude of the EEG as a criterion in assessing the brain activity comprising:

sampling means for sampling electrical signals derived from plural EEG channels at regular time intervals from both sides of the head of a patient and holding the samples;

analog to digital conversion means connected to receive the samples held successively by the sampling means and producing therefrom digital outputs representing the magnitudes of the samples;

a digital computer programmed to receive the digital outputs associated with each of said plural EEG channels in succession from the analog to digital conversion means and having means for processing substantially simultaneously the digital outputs from each of the plural EEG channels including:

means for comparing digital outputs from each with a threshold value;

means for determining a time interval between a current digital outputs and immediately preceding digital outputs which exceed the threshold value, and means for accumulating a total of time intervals exceeding a minimum duration during a particular time period and generating signals representative of total time intervals accumulated during consecutive time periods; and display means for displaying side by side the representative signals for each channel.

14. Apparatus according to claim 13 wherein the representative signals represent the mean duration of the time intervals exceeding a minimum duration during the time period.

15. Apparatus according to claim 13 wherein the determining means is reset immediately after determining a time interval and is restarted when a subsequent sample is detected below the threshold value.

16. Apparatus according to claim 13 wherein the digital computer stores local maximum and minimum values for analysis and display.

17. Apparatus according to claim 13 wherein the computer includes:

means for calculating the mean of the squares of the sample amplitudes, means for counting the number of time intervals of at least the minimum duration which occur in a time period, and means for performing statistical analysis of calculated and counted values.

18. A method of analyzing an electro-encephalogram (EEG) in which the amplitude of the EEG is used as a criterion in assessing the brain activity, wherein the EEG is represented by a plurality of digital values respectively corresponding to the amplitude of the EEG signal at a succession of instants spaced apart by predetermined equal time periods, comprising:

comparing sequentially the digital values with a threshold value;

indicating whether or not the digital values exceed the threshold value, measuring each time interval during which successive digital values are smaller than the threshold value;

summing the measurements of the time intervals having at least a certain minimum duration during an extended time period to provide a total of the measurements for each of a plurality of consecutive extended time periods; and producing an output display dependent on the totals of the measurements.

19. A method according to claim 18 wherein the measurement of time durations is performed in response to signals from a clock oscillator which controls the application of digital values for comparison.

20. A method according to claim 18 further comprising:
graphically displaying the values of a plurality of the totals represented on a rectangular or other type of coordinate system.

21. A method according to claim 18 further comprising:
determining the mean of the squares of the digital values occurring during an extended time period.

22. A method according to claim 18 further comprising:
counting the number of time intervals added to the total during an extended time period, and
calculating the mean duration of the time intervals during the period.

* * * * *